United States Patent
Abitabilo et al.

(10) Patent No.: US 10,772,611 B2
(45) Date of Patent: Sep. 15, 2020

(54) NEEDLE ASSEMBLY WITH FLEXIBLE CATHETER NOSE FOR DIAGNOSTIC SAMPLING OF FLUID

(71) Applicant: Smiths Medical ASD, Inc., Plymouth, MN (US)

(72) Inventors: James Edward Abitabilo, Bristol, CT (US); Jay T. Breindel, Branford, CT (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days.

(21) Appl. No.: 16/303,535

(22) PCT Filed: May 19, 2017

(86) PCT No.: PCT/US2017/033478
§ 371 (c)(1),
(2) Date: Nov. 20, 2018

(87) PCT Pub. No.: WO2017/201369
PCT Pub. Date: Nov. 23, 2017

(65) Prior Publication Data
US 2019/0357892 A1    Nov. 28, 2019

Related U.S. Application Data

(60) Provisional application No. 62/339,287, filed on May 20, 2016.

(51) Int. Cl.
*A61B 10/02*    (2006.01)
*A61B 5/15*    (2006.01)
(Continued)

(52) U.S. Cl.
CPC ........ *A61B 10/0233* (2013.01); *A61B 5/1405* (2013.01); *A61B 5/150992* (2013.01);
(Continued)

(58) Field of Classification Search
None
See application file for complete search history.

(56) References Cited

U.S. PATENT DOCUMENTS

| 4,317,445 A | 3/1982 | Robinson |
| 4,994,034 A * | 2/1991 | Botich ............... A61M 5/3129 |
| | | 604/110 |

(Continued)

FOREIGN PATENT DOCUMENTS

| EP | 0451040 A1 | 10/1991 |
| EP | 2764885 A1 | 8/2014 |

(Continued)

OTHER PUBLICATIONS

International Search Report for corresponding International Application No. PCT/US2017/033478 dated Aug. 29, 2017; 6 pages.

(Continued)

*Primary Examiner* — Matthew Kremer
*Assistant Examiner* — Samuel C Kim
(74) *Attorney, Agent, or Firm* — Patterson Thuente Pedersen, P.A.

(57) ABSTRACT

A needle assembly for sampling fluid from a patient including a needle guard, an insertion needle, and a needle housing. The distal end of the needle guard includes a nose portion and a flexible nose extension defining a fluid collection reservoir. The proximal end of the needle guard includes a push feature. The insertion needle has a sharpened distal tip, a proximal needle end and a shaft defining a lumen extending therebetween. The needle housing is operably coupled to the proximal needle end and is slideably coupled to the needle guard. The needle housing includes a flash chamber including a wall defining a cavity. The cavity is in fluid communication with the lumen of the insertion needle and is sealed at one end by a gas permeable flash plug. The push feature selectively engages the flash plug to divert (Continued)

captured bodily fluids to the fluid collection reservoir for sampling.

8 Claims, 6 Drawing Sheets

(51) Int. Cl.
    *A61B 5/145*     (2006.01)
    *A61M 25/06*     (2006.01)
    *A61B 10/04*     (2006.01)

(52) U.S. Cl.
    CPC ......... *A61B 10/04* (2013.01); *A61M 25/0612* (2013.01); *A61B 2010/045* (2013.01)

(56) References Cited

U.S. PATENT DOCUMENTS

| | | | |
|---|---|---|---|
| 5,000,740 | A | 3/1991 | Ducharme et al. |
| 5,195,983 | A | 3/1993 | Boese |
| 5,368,029 | A | 11/1994 | Holcombe et al. |
| 5,531,720 | A | 7/1996 | Atkins |
| 5,558,641 | A | 9/1996 | Glantz et al. |
| 5,676,658 | A | 10/1997 | Erskine |
| 5,989,229 | A | 11/1999 | Chiappetta |
| 6,213,978 | B1 | 4/2001 | Voyten |
| 6,547,762 | B1 | 4/2003 | Botich et al. |
| 6,585,703 | B1 | 7/2003 | Kassel et al. |
| 6,719,726 | B2 | 4/2004 | Meng et al. |
| 6,872,193 | B2 | 3/2005 | Shaw et al. |
| 6,972,002 | B2 | 12/2005 | Thorne |
| 7,785,299 | B2 | 8/2010 | Crawford et al. |
| 8,383,044 | B2 | 2/2013 | Davis et al. |
| 8,535,257 | B1 | 9/2013 | Zelten et al. |
| 8,728,038 | B2 * | 5/2014 | Spearman ........ A61B 5/150992 600/468 |
| 9,114,231 | B2 | 8/2015 | Woehr et al. |
| 9,393,382 | B2 | 7/2016 | Heck |
| 9,399,116 | B2 | 7/2016 | Goral et al. |
| D808,013 | S | 1/2018 | Chheda et al. |
| 10,028,691 | B2 | 7/2018 | Goral et al. |
| D844,774 | S | 4/2019 | Akcay et al. |
| 10,548,522 | B2 | 2/2020 | Akcay et al. |
| 2002/0165496 | A1 | 11/2002 | Thompson |
| 2003/0083621 | A1 | 5/2003 | Shaw et al. |
| 2003/0199827 | A1 | 10/2003 | Thorne |
| 2005/0182363 | A1 | 8/2005 | Kulli |
| 2005/0273019 | A1 | 12/2005 | Conway et al. |
| 2007/0167917 | A1 | 7/2007 | Lee |
| 2007/0191776 | A1 | 8/2007 | Bialecki et al. |
| 2008/0097330 | A1 | 4/2008 | King et al. |
| 2008/0097344 | A1 | 4/2008 | McKinnon et al. |
| 2008/0300543 | A1 | 12/2008 | Abriles et al. |
| 2009/0088696 | A1 | 4/2009 | Harding et al. |
| 2010/0191189 | A1 | 7/2010 | Harding et al. |
| 2011/0319825 | A1 * | 12/2011 | Goral ................ A61M 25/0097 604/164.01 |
| 2012/0197204 | A1 | 8/2012 | Helm, Jr. |
| 2013/0317426 | A1 | 11/2013 | Fiser et al. |
| 2014/0046272 | A1 | 2/2014 | Erskine |
| 2014/0052021 | A1 | 2/2014 | Burkholz et al. |
| 2014/0128775 | A1 | 5/2014 | Andreae et al. |
| 2014/0276458 | A1 | 9/2014 | Mansour et al. |
| 2014/0276462 | A1 | 9/2014 | Vincent et al. |
| 2015/0224267 | A1 | 8/2015 | Farrell et al. |
| 2016/0135841 | A1 | 5/2016 | Albert et al. |
| 2016/0220762 | A1 | 8/2016 | Goral et al. |
| 2016/0220791 | A1 | 8/2016 | Akcay et al. |
| 2017/0239443 | A1 | 8/2017 | Abitabilo et al. |
| 2018/0296149 | A1 | 10/2018 | Goral et al. |
| 2019/0314614 | A1 | 10/2019 | Krause et al. |
| 2019/0314615 | A1 | 10/2019 | Johnson et al. |
| 2020/0009366 | A1 | 1/2020 | Abitabilo et al. |

FOREIGN PATENT DOCUMENTS

| | | |
|---|---|---|
| KR | 10-2008-0019633 | 3/2008 |
| WO | WO 96/032148 A1 | 10/1996 |
| WO | WO 03/043496 A2 | 5/2003 |
| WO | WO 2004/050138 A2 | 6/2004 |
| WO | WO 2006/086849 A1 | 8/2006 |
| WO | WO 2014/143220 A1 | 9/2014 |
| WO | WO 2015/123689 A1 | 8/2015 |
| WO | WO 2017/029374 A1 | 2/2017 |
| WO | WO 2019/079719 A1 | 4/2019 |

OTHER PUBLICATIONS

Written Opinion of the International Searching Authority for corresponding International Application No. PCT/US2017/033478 dated Aug. 29, 2017; 4 pages.
Search Report and Written Opinion dated May 17, 2016 for PCT Application No. PCT/US2016/015972, 14 pages.
Search Report and Written Opinion dated May 17, 2016 for PCT Application No. PCT/US2016/015975, 11 pages.
Search Report and Written Opinion dated Jun. 1, 2016 for PCT Application No. PCT/US2016/015958, 12 pages.
Search Report and Written Opinion dated Jun. 2, 2016 for PCT Application No. PCT/US2017/018350, 11 pages.
Search Report and Written Opinion dated Jul. 23, 2019 for PCT Application No. PCT/US2019/026467, 11 pages.
Search Report and Written Opinion dated Feb. 1, 2019 for PCT Application No. PCT/US2018/056711, 12 pages.
Search Report and Written Opinion dated Jul. 22, 2019 for PCT Application No. PCT/US2019/026469, 16 pages.
Written Opinion dated Oct. 16, 2017 for PCT Application No. PCT/US2017/040887, 7 pages.
Search Report dated Oct. 16, 2017 for PCT Application No. PCT/US2017/040887, 4 pages.
Communication dated Jul. 18, 2019 for EP Application No. 16744275.5, 7 pages.
Communication dated Aug. 7, 2018 for EP Application No. 16744268.0, 7 pages.
Communication dated Jan. 3, 2020 for EP Application No. 17753917.8, 7 pages.
Office Action dated Jun. 22, 2018 for Australian Application No. 2016211195, 2 pages.
Office Action dated Sep. 3, 2019 for Chinese Application No. 201680008123.7, 16 pages.
Office Action dated Apr. 7, 2020 for Chinese Application No. 201680008123.7, 12 pages.

* cited by examiner

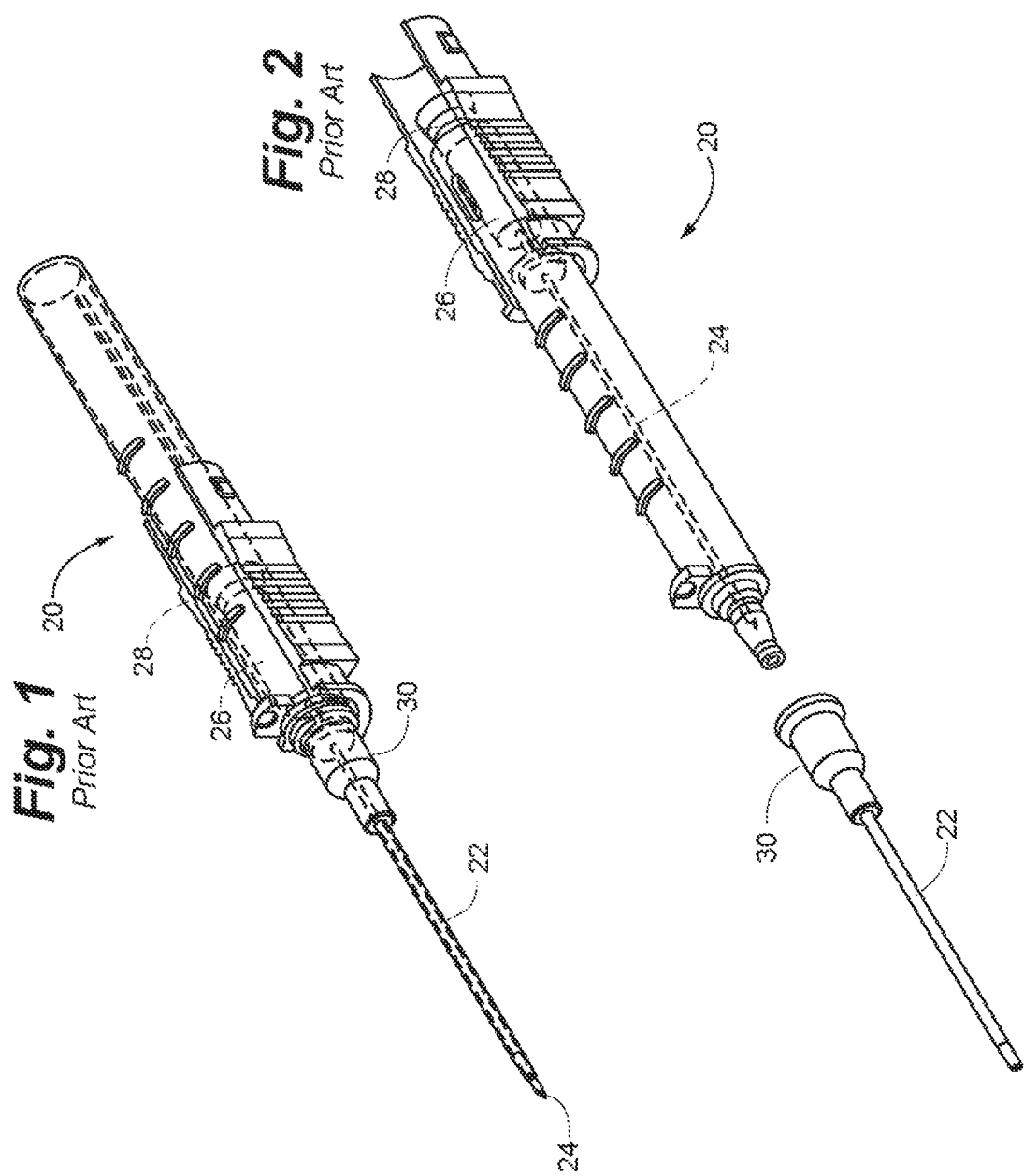

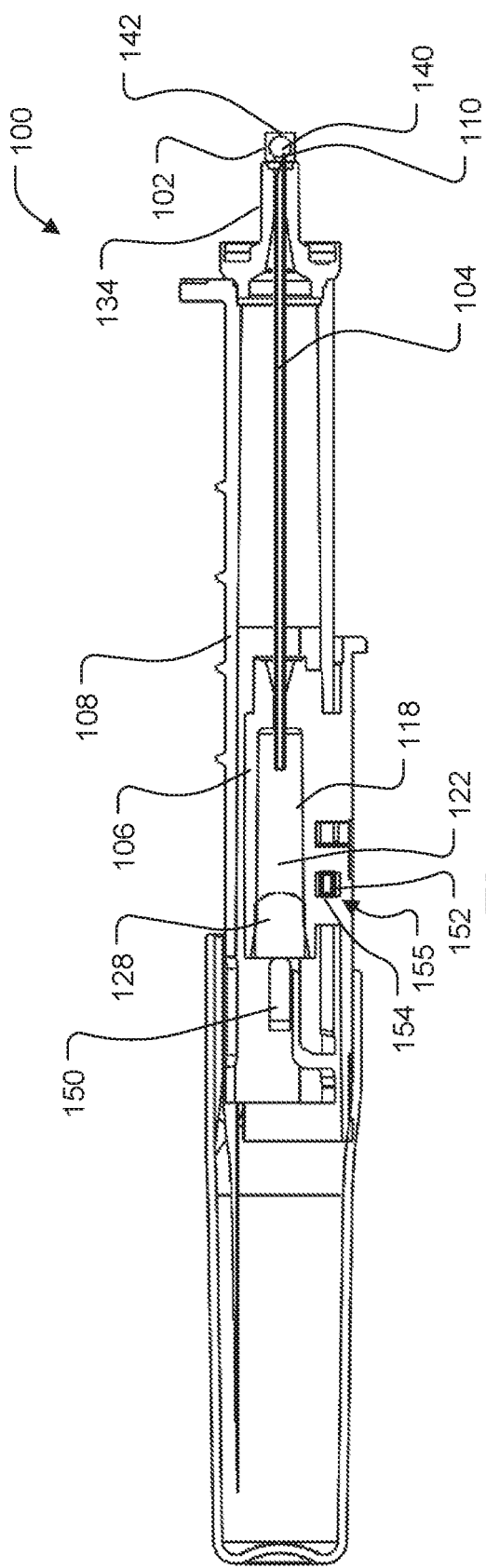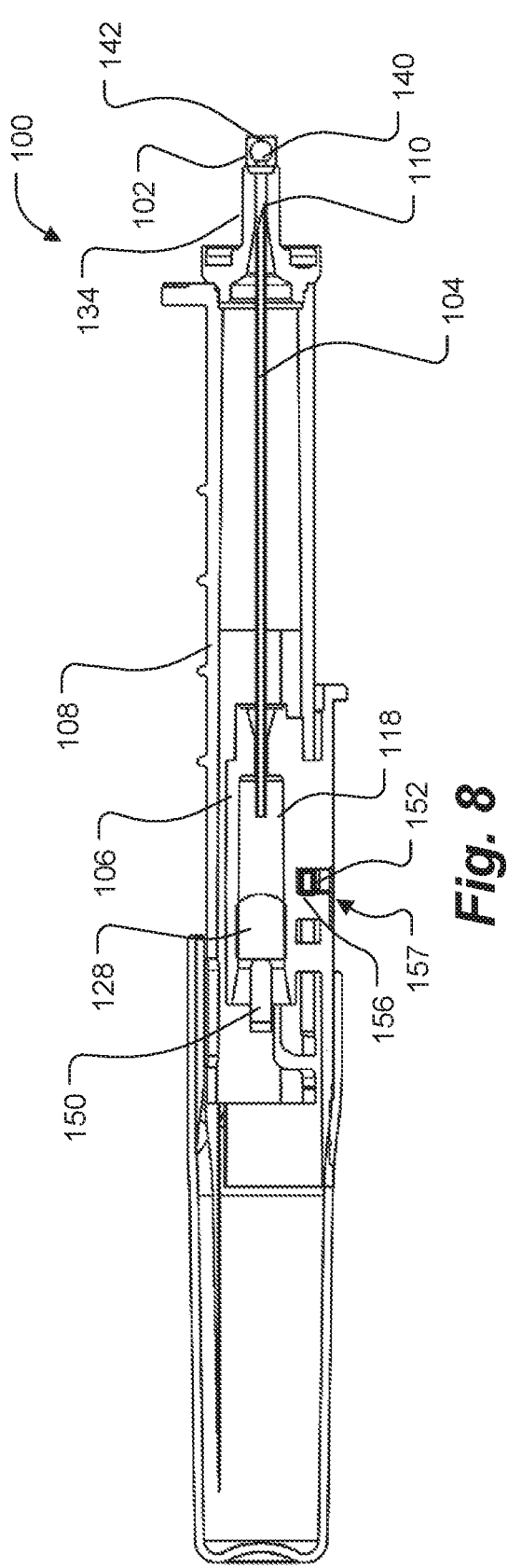

NEEDLE ASSEMBLY WITH FLEXIBLE CATHETER NOSE FOR DIAGNOSTIC SAMPLING OF FLUID

RELATED APPLICATION INFORMATION

The present application is a National Phase entry of PCT Application No. PCT/US2017/033478, which claims the benefit of U.S. Provisional Application No. 62/339,287 filed May 20, 2016, which are hereby incorporated herein in their entirety by reference.

TECHNICAL FIELD

The present disclosure relates generally to needle assemblies, and more particularly to safety needle assemblies having diagnostic sampling features that provide controlled access to blood or bodily fluid captured by the needle assemblies for testing and analysis.

BACKGROUND

Various types of intravenous (IV) therapy have been used to administer medical fluids and withdraw bodily fluids from patients. IV therapy has been used for purposes such as maintenance of fluid and electrolyte balance, transfusion of blood, administration of nutritional supplements, chemotherapy, and administration of drugs and medications. Specifically, fluids have been administered intravenously by injection through a hypodermic needle, or intermittently or continuously by infusion using a needle or catheter. The most common intravenous access method utilized by clinicians has been the peripheral IV catheter.

Peripheral IV catheters are made of soft, flexible plastic or silicone, generally between fourteen to twenty-four gauge in size. In conventional venipuncture procedures, a catheter is inserted into a vein in the patient's hand, foot, or the inner aspect of the arm or any vein in the body that will accept an IV catheter. In order to properly place the IV catheter into a patient's vein, a sharp introducer needle is used to puncture the skin, tissue, and vein wall to provide a path for placement of the catheter.

Referring to FIGS. 1 and 2, a prior art conventional IV safety needle assembly 20, configured for insertion of an "over-the needle" catheter 22, is depicted. The catheter 22 is operably coupleable to the safety needle assembly 20, in part by positioning the catheter 22 coaxially over the needle 24 of the safety needle assembly 20. The catheter 22 thus rides with the needle 24 through the skin, tissue, and vein wall and into the patient's vein. Often, the insertion end of the catheter 22 is tapered in an effort to minimize the amount of force required to insert the catheter 22 into the biological site.

The catheter 22 can include a catheter hub 30, which can be selectively coupled to a portion of the safety needle assembly 20. Catheter hub 30 is sometimes configured to control the flow of fluid through the catheter 22 via an internal fluid passageway that runs substantially parallel to the longitudinal axis of the catheter hub 30. In some embodiments, the fluid passageway includes a septum or valve to enable sealing of the fluid passageway to restrict or prevent bodily fluid from leaking out of the catheter hub 30 when the catheter 22 is inserted into a patient's vein and the needle 24 is removed.

When the needle 24 pierces the vein, blood will "flashback" through the needle 24 and into the flash chamber 26. Thus, once the clinician observes this flashback of blood, the clinician will know that the catheter 22 and needle 24 have been inserted in the vein. The catheter 22 can be advanced further into the vein as desired and the needle 24 can then be withdrawn from the catheter 22.

In addition to placement of an IV catheter, samples of the patient's blood are often obtained (e.g., for testing, blood typing or other analysis of a patient's condition). Such analysis frequently involves testing the blood for the presence of certain characteristics, such as the presence or amount of one or more constituents, or to determine the level of one or more parameters. For many of these blood tests, only a small sample of blood is required. After the IV catheter has been inserted, the clinician may obtain a blood sample through a variety of methods. One method is to have the patient endure another needle stick either by a needle and syringe to draw an aliquot of blood, or by pricking the patient's finger with a lancet for a few drops of blood.

Because some IV catheters of the prior art include an integrated flash chamber 26, another method is to enable access to the blood within the flash chamber 26 after the catheter 22 and needle 24 have been inserted into the patient's vein. Usually the proximal end of the flash chamber 26 is blocked by a flash plug 28. The flash plug 28 typically includes a filter material that enables air to vent from the flash chamber as the blood or fluid fills the chamber, but inhibits the blood or fluid from passing from the flash chamber 26.

SUMMARY OF THE DISCLOSURE

Embodiments of the present disclosure relate to needle assemblies and methods that include a needle guard with a flexible nose extension having a fluid collection reservoir that is able to receive a small quantity of bodily fluid from the flashback chamber of the needle assembly using integral features for controlled bodily fluid sample distribution.

Some embodiments provide a needle assembly for sampling fluid from a patient including a needle guard, an insertion needle, and a needle housing. The needle guard has a distal end and a proximal end. The distal end of the needle guard includes a nose portion and a flexible nose extension defining a fluid collection reservoir. The proximal end of the needle guard includes a push feature. The insertion needle has a sharpened distal tip, a proximal needle end and a shaft defining a lumen extending there between. The needle housing is connected to the proximal needle end and is slideably coupled to the needle guard. The needle housing includes a flash chamber including a wall defining a cavity. The cavity is in fluid communication with the lumen of the insertion needle and is sealed at one end by a gas permeable flash plug. The needle housing is moveable between an extended position in which the sharpened distal tip is exposed for insertion and one or more retracted positions in which the sharpened distal tip is concealed within the needle guard. The push feature selectively engages the flash plug to divert captured bodily fluids to the fluid collection reservoir for sampling, when the needle housing is in one of the retracted positions.

Some embodiments can include a flexible nose extension with an external seal through which captured bodily fluids can be expressed when the flexible nose extension is deformed. In some embodiments, a catheter hub is operably coupled to the nose portion of the needle guard in the extended position.

Some embodiments of a needle assembly include a lock mechanism that restricts distal movement of the needle housing after the push feature engages the flash plug and diverts captured bodily fluids to the fluid collection reservoir. Some embodiments of a needle assembly include a two step locking arrangement for restricting distal movement of the needle housing that includes a first lock and a second lock. Further, the first lock can be configured to restrict distal movement of the needle housing prior to the push feature engaging the flash plug and the second lock can be configured to restrict distal movement after the push feature has engaged the flash plug and diverted captured bodily fluids to the fluid collection reservoir for sampling. Further, engaging the second lock can require a different type of user motion than required to engage the first lock.

In some embodiments, the one or more retracted positions include a partially retracted position and a fully retracted position. Further, in some embodiments, the needle housing is moveable in a proximal direction between: the extended position; the partially retracted position wherein the sharpened distal tip of the insertion needle is withdrawn into the needle guard and the push feature has not yet begun to engage the gas permeable flash plug; and the fully retracted position in which the push feature has engaged the gas permeable flash plug and urged fluid from the flash chamber into the fluid collection reservoir of the flexible nose extension and the needle housing is prevented from further sliding movement. Further, the fluid collection reservoir may be deformed to open a seal and provide trapped fluid from the flexible nose extension for analysis.

Some embodiments are directed to a method of sampling a bodily fluid from a patient with a needle assembly. The method includes providing a needle assembly including: a needle guard including a flexible nose extension defining a fluid collection reservoir at a distal end of the needle guard and a push feature at a proximal end of the needle guard; an insertion needle having a lumen and a sharpened distal tip; and a needle housing operably coupled to a proximal end of the insertion needle and slideably coupled to the needle guard, the needle housing including a flash chamber in fluid communication with the insertion needle and sealed at one end by a flash plug. The method includes inserting the insertion needle to access bodily fluid that is provided through the lumen to the flash chamber and retracting the needle housing until the sharpened distal tip of the insertion needle is located within the needle guard. The method further includes retracting the needle housing so that the push feature contacts the flash plug of the flash chamber and provides the bodily fluid back out the lumen into the fluid collection reservoir of the flexible nose extension. The method also includes distorting the flexible nose extension to open a seal and express the bodily fluid of the fluid collection reservoir in a controlled fashion.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 1 is a perspective view depicting a peripheral intravenous catheter of the prior art in a first position.

FIG. 2 is a perspective view depicting the peripheral intravenous catheter of the prior art of FIG. 1 in a second position.

FIG. 7 is a side cross sectional view depicting a safety needle assembly where the needle is in a partially retracted position, according to an embodiment.

FIG. 8 is a side cross sectional view depicting a safety needle assembly where the needle is in a fully retracted position, according to an embodiment.

Figure 3:
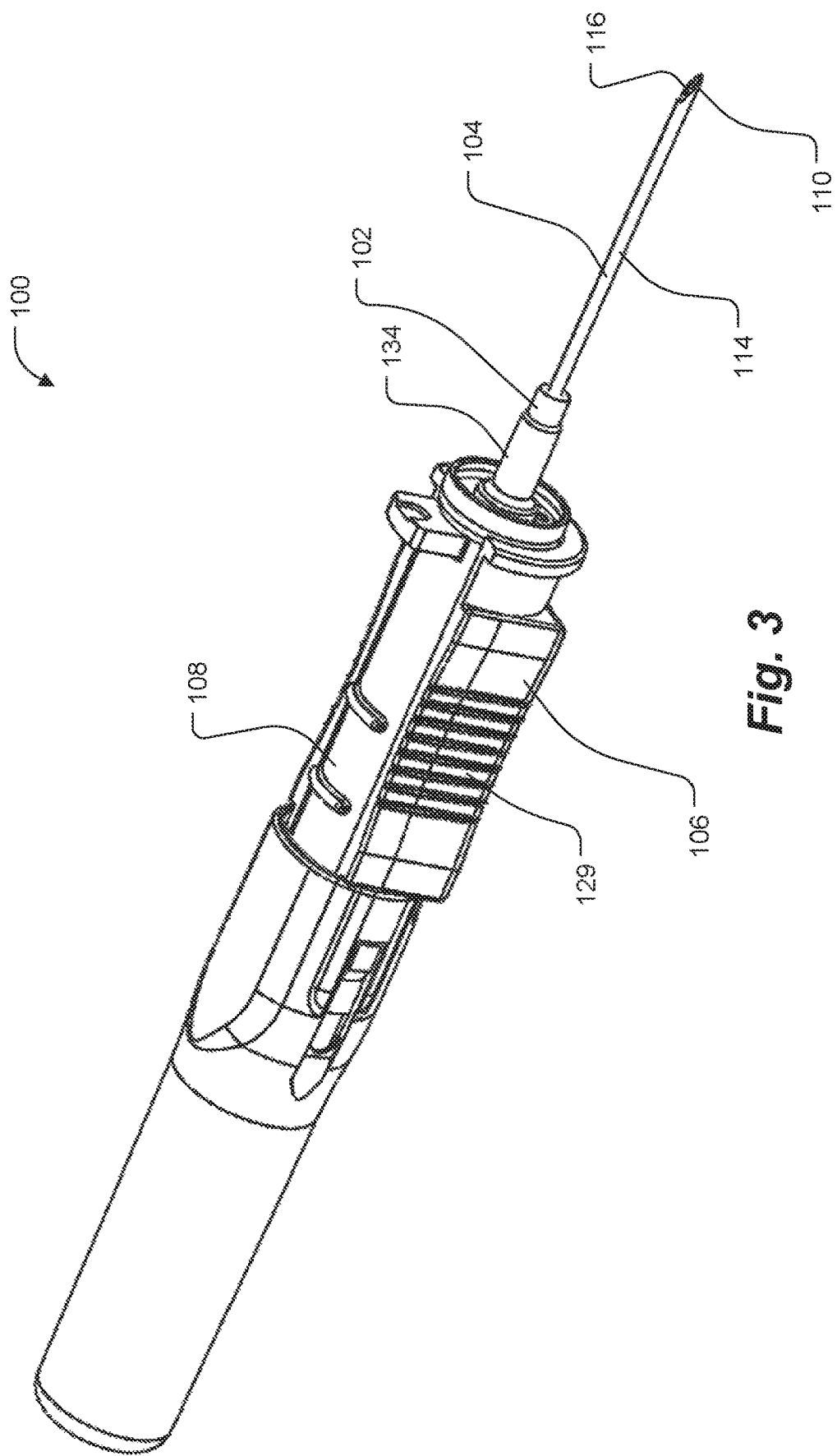
FIG. 3 is a perspective view depicting a safety needle assembly where the needle is in a fully extended position, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIGS. 1 and 2 show a safety needle assembly 20 according to the prior art. Details of safety needle assembly 20 are set forth in the background section above. Use of a peripheral device, such as the catheter 22 and its catheter hub 30, with the safety needle assemblies 100 disclosed in FIGS. 3-9 are contemplated, although these components are not shown in the figures for clarity of the other features of the needle assemblies 100 being depicted.

Figure 4:
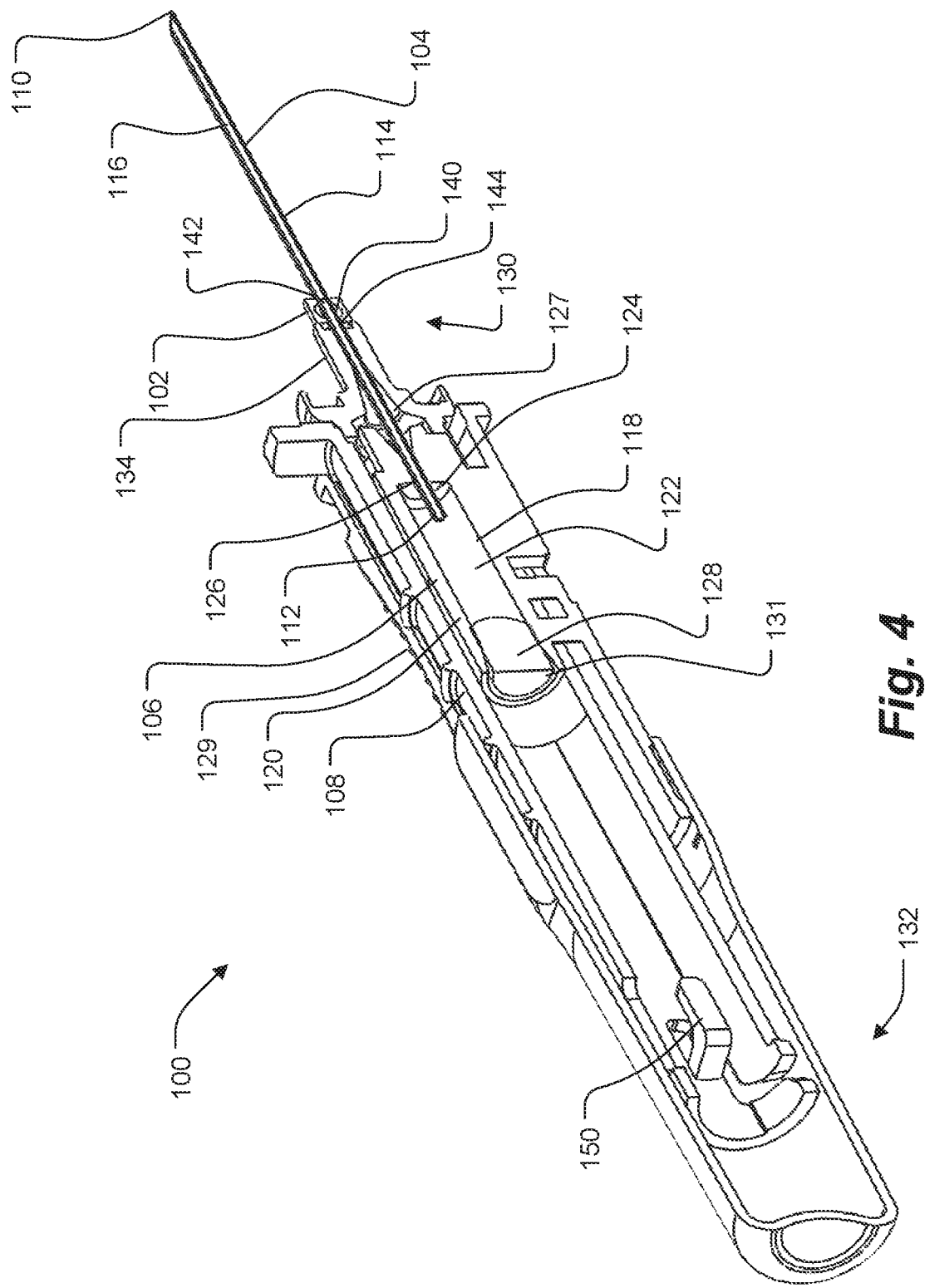
FIG. 4 is a cross-sectional perspective view depicting a safety needle assembly where the needle is in a fully extended position, according to an embodiment.

FIGS. 3-4 set forth a safety needle assembly 100 that includes a flexible nose extension 102 for diagnostic sample collection and sealing. Needle assembly 100 generally includes an insertion needle 104, a needle housing 106, and a needle guard 108. Insertion needle 104 has a sharpened distal tip 110, a proximal end 112 and a shaft 114 defining a lumen 116 extending therebetween.

Needle housing 106 is operably coupled to the proximal end 112 of the insertion needle 104. The needle housing 106 includes a flash chamber 118 comprising a wall 120 defining a cavity 122. In some embodiments, the wall 120 defining the cavity 122 can be constructed of a transparent material to enable a clinician to visually see when fluid enters the cavity 122.

The cavity 122 is in fluid communication with the lumen 116 of the insertion needle 104, according to exemplary embodiments. The distal end 124 of the flash chamber 118 can include an aperture 126 that is sized to accommodate the proximal end 112 of the insertion needle 104. The cavity 122 can be sealed by a gas permeable flash plug 128. For example, in some embodiments, the proximal end 131 of cavity 122 can be plugged with a microporous flash plug 128. Flash plug 128 can be comprised of a material that enables air to vent from the cavity 122 as fluid fills the cavity 122, while inhibiting the fluid from passing through the flash plug 128 and out of the cavity 122. Needle housing 106 further includes a grip portion 129 located on the outside of the needle guard 108. The grip portion 129 enables a user to slide back the needle housing 106 in relation to the needle guard 108 with his/her fingers.

Needle guard 108 has a distal end 130 and a proximal end 132. Distal end 130 of needle guard 108 can be configured with a tapered blunt tip or "nose" 134 which further includes a flexible nose extension 102 at its tip. Passageway 127 extends through the distal end 130 of the needle guard 108, including the nose 134 through which an insertion needle 104 can pass. Further, insertion needle 104 can pass through the perforations or openings present in the walls of the nose extension 102. In some versions, safety needle assembly 100 can include a catheter hub coupling mechanism (not shown) to selectively couple a catheter hub, such as catheter hub 30, for example.

Figure 5:
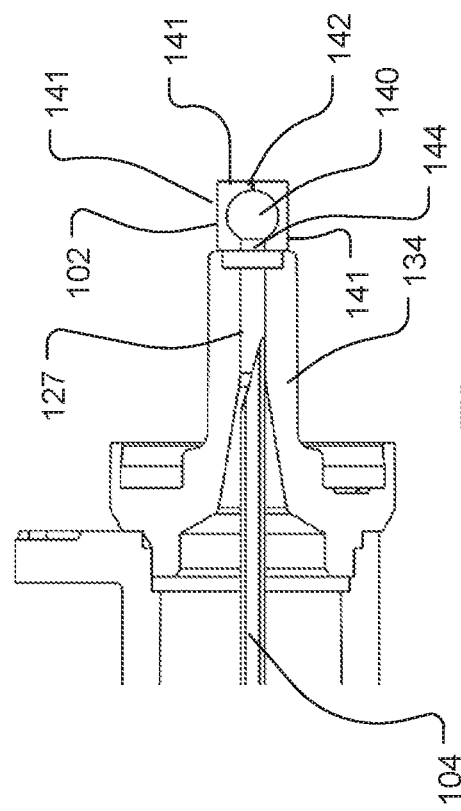
FIG. 5 is a close up side cross sectional view depicting the nose and flexible nose extension of a safety needle assembly where the insertion needle is retracted within the nose, according to an embodiment.

Nose extension 102 is generally a flexible elastomeric protrusion that features a central sample collection reservoir 140 defined by outer walls 141 that include at least an outer seal 142, as shown in the example embodiment of FIG. 5. The outer surface of nose extension 102 can be various shapes, such as a cylinder or prism, for example. The nose extension 102 facilitates continuation of a sealable passageway 127 that extends from aperture 126, through which an insertion needle 104 can readily pass. Insertion needle 104 spans the width of nose extension 102 when the needle 104 is in the extended position. The insertion needle 104 is fully removed from the nose extension 102 when the needle 104 is in the fully retracted position, as can be seen in greater detail in the up close view of the nose 134 and flexible nose extension 102 of FIG. 5. The contours of the outer walls 141 can form and take on various shapes (i.e. flat, curved, round, rectangular, etc.) but can be compact enough in profile, in some embodiments, such that the nose extension 102 can fit within the confines of a catheter hub mounted on the nose 134 of the needle assembly 100.

The sample collection reservoir 140 of the nose extension 102 can be a cavity of various sizes, however, it can generally be sized to accommodate a volume equivalent to a few drops of blood or fluid. The outer seal 142 generally provides an annular opening in close contact with the perimeter of insertion needle 104 when the needle is present. When the insertion needle 104 is not present, the opening is closed and a fluid-tight joinder of the elastomeric material of nose extension 102 is formed. Opposite the outer seal 142 on flexible nose extension 102 is an inner aperture 144 located adjacent to the nose 134 and its central passageway 127. Aperture 144 generally provides a tight seal around insertion needle 104, when present. However, when insertion needle 102 is retracted from the aperture 144, the opening provided is generally wide enough such that it will not completely close and, accordingly, leaves the passageway 127 of nose 134 in open communication with the fluid collection reservoir 140.

Needle guard 108 can be slideably coupled to the needle housing 106. For example, in one embodiment, needle housing 106 can have a "C" shaped cross section conformed to fit around the outer surface of the needle guard 108 in a manner that inhibits the needle housing 106 from readily separating from the needle guard 108, yet enables the needle housing 106 to slide along the longitudinal axis of the needle guard 108 with minimal resistance.

In some embodiments, the needle guard 108 can include structure defining a groove (not shown), and the needle housing 106 can be configured to slide along the groove, thereby inhibiting the needle housing 106 from rotating about the longitudinal axis of the needle guard 108. In one version, the needle housing 106 can include a lug configured to fit within the groove of the needle guard 108, thereby enabling linear movement of the needle housing 106 substantially parallel to the longitudinal axis of the needle guard 108, but restricting rotational movement of the needle housing 106 relative to the needle guard 108.

Figure 6:
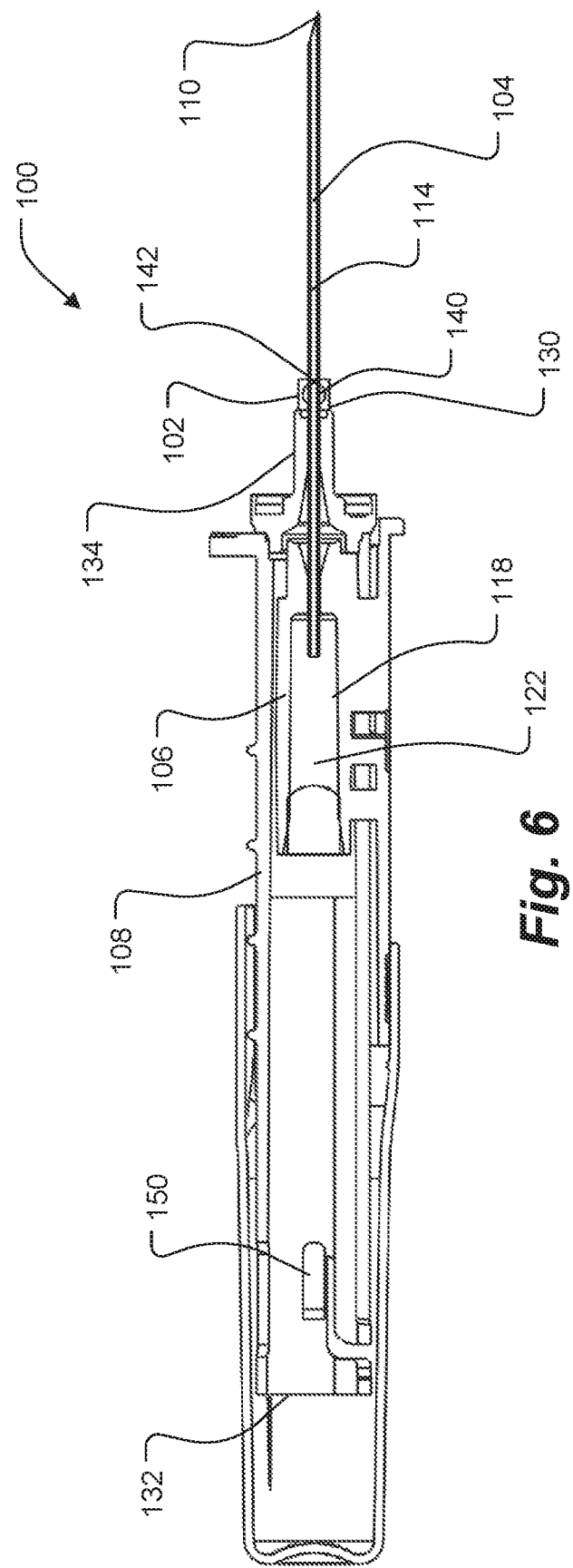
FIG. 6 is a side cross sectional view depicting a safety needle assembly where the needle is in a fully extended position, according to an embodiment.

Needle guard 108 can be moveable between an initial extended position (as depicted in FIGS. 3, 4, and 6), wherein the sharpened distal tip 110 extends from the needle guard 108 and one or more retracted positions. The retracted positions can include a (first) partially retracted position (as depicted in FIG. 7), wherein the sharpened distal tip 110 is retracted back to the nose extension portion of the needle guard 108, and a (second) fully retracted position (as depicted in FIG. 8), wherein the sharpened distal tip 110 is housed within the needle guard 108. In the initial extended position, when a catheter 22 is operably coupled to the needle guard 108, a portion of the insertion needle 104 can extend through aperture 126, passageway 127, and catheter 22, such that the sharpened distal tip 110 of insertion needle 104 protrudes slightly from the catheter 22. In the retracted positions, the insertion needle 104 is withdrawn from the catheter 22 and the sharpened distal tip 110 is housed by the needle guard 108 in a manner intended to reduce or eliminate the likelihood of an inadvertent needle stick.

In some embodiments, the insertion needle 104 can be locked in position relative to the needle guard 108. Several different types of locks and locking mechanisms can be used for this purpose, including single stage or multi-stage lock arrangements.

In one embodiment, the needle guard 108 defines a groove and can define a bottleneck that has a narrower width than the groove. A wedge shaped lug of the needle housing 106 can include an apex that faces the bottleneck in the first position. When the needle housing 106 is slid into the first or second retracted position, the apex of the wedge comes into contact with the bottleneck. As the bottleneck has a width narrower than that of the wedge, it will initially resist movement through the bottleneck. With sufficient force, the wedge will cause the bottleneck to temporarily deform, thereby enabling the lug to pass through the bottleneck. Thereafter, the lug will be unable to pass back through the bottleneck in the opposite direction, and the insertion needle 104 will be locked in position relative to the needle guard 108.

Multiple locks, lock locations, or lock mechanisms may be possible within the same embodiment as well. For example, this may permit locking the needle housing 106 in two separate locations to accommodate the desired operation of the needle. For example, in FIG. 7, a lock mechanism 152 on needle guard 108 is shown interacting with a first lock triangle 154 that is present in the needle housing 106, to provide a first lock 155. Further, in FIG. 8, the lock mechanism 152 on the needle guard 108 is shown interacting with a second lock triangle 156 that is present on the needle housing 106, to provide a second lock 157. It should be understood, however, that embodiments containing only a single lock (for example, which only contain a lock 157 in the fully retracted position) are contemplated by these figures and disclosure as well.

In FIG. 4, the proximal end 132 of the needle guard 108 includes a push feature 150. Push feature 150 can take on various shapes and mechanisms. In general, the push feature 150 provides a rigid or moveable structure which can provide a force against the flash plug 128 to control the flow of fluid in the flash chamber 118 to the collection reservoir 140. In FIG. 4, a finger-like projection extends outwardly from the wall of the needle guard 108 before bending to a generally perpendicular orientation and extending in a generally axial direction for a short distance within the needle guard 108. This projection provides a rigid bar that is shown and referred to as the push feature 150. Accordingly, in this embodiment, the rigid bar is designed so that it will contact the flash plug 128 as the insertion needle 104 is withdrawn into the needle guard 108.

FIGS. 6-9 demonstrate an embodiment of the operation of the safety needle assembly 100, including obtaining blood or bodily fluid for diagnostic testing. In FIG. 6, the insertion needle 104 is in the fully extended position which provides a section of the shaft 114 beyond the needle guard 108. This configuration is generally the initial state (i.e. "extended position") of the safety needle assembly 100 which is used to insert a peripheral catheter or similar device (see catheter 22 and catheter hub 30 in FIGS. 1 and 2, for example). Specifically, the needle housing 106 is extended forward into its distal-most position with respect to the needle guard 108. The shaft 114 of the insertion needle 104 passes from the needle housing 106, through the aperture 126, through the nose 134, through the nose extension 102, and out the distal end 130 of the needle guard 108. The outer seal 142 of the nose extension 102 is engaged around the shaft 114 of the insertion needle 104 to provide a fluid-tight barrier. The cavity 122 of the flash chamber 118 is empty in this initial state and flash plug 128 is not engaged to the push feature 150 that is located near the proximal end 132 of the needle guard 108.

Although not shown in FIG. 6, a catheter 22 and catheter hub 30, similar to those shown in FIGS. 1 and 2, can be mounted to the needle assembly 100 in the ready position for placement, in some embodiments. Specifically, the internal passageway of the catheter hub 30 can be mounted over the insertion needle 104, nose 134, and nose extension 102. Further, the insertion needle 104 can fully extend through the catheter 22 such that the sharpened distal tip 110 is exposed for patient insertion.

Prior to patient insertion and placement of the catheter 22 from a needle assembly 100, preparation of the biological site of the patient is generally needed. A tourniquet can be applied proximal to the biological site and a variety of techniques can be used to dilate the patient's vein. While wearing disposable gloves, a clinician cleanses the biological site and a vein is retracted or anchored by placing a thumb over the vein distal to the site. The needle 104 and catheter 22 are introduced into the vein by inserting the bevel of the sharpened distal tip 110 into the vein at about a 20-30 degree angle with the bevel facing up in order to pierce one wall of the vein. If successful, blood from the vein will flow through the lumen 116 of the needle 104 and into the flash chamber 118, thereby indicating that the vein has been entered.

Referring to FIG. 7, a subsequent position (i.e. "first retracted position" or "partially retracted position") of the needle assembly 100 is shown. Just prior to moving to this position, after needle insertion and flashback of fluid into the flash chamber 118, the user can perform partial withdrawal of the insertion needle 104. Namely, placement of the insertion needle 104 is finished when the safety needle assembly 100 is lowered towards the skin to decrease the entry angle, and the catheter 22 is advanced slightly into the vein. The insertion needle 104 is loosened and the catheter 22 is gently advanced farther up into the vein until the catheter hub 30 of the catheter 22 is against the biological site. The tourniquet is loosened and the insertion needle 104 is withdrawn from the catheter 22, as the needle housing 106 is retracted from the extended position. The subsequent configuration is shown in FIG. 7. Specifically, a cross section of a safety needle assembly 100 having a partially retracted needle 104 is shown in FIG. 7. The needle housing 106 and the corresponding needle 104 are shown proximally shifted within the needle guard 108 compared with FIG. 5. The distal tip 110 of the needle 104 has passed through the outer seal 142 of the nose extension 102 and is shown partially extending into the collection reservoir 140. The outer seal 142 of the nose extension 102 forms a seal at the very distal tip of the needle guard 108. In FIG. 7, the push feature 150 is close to initiating contact with the flash plug 128.

In some embodiments, as generally depicted in FIG. 7, a lock 155 is present in this position for restricting distal movement of the needle housing 106. Specifically, the lock 155 is configured to restrict distal movement of the needle housing prior to the push feature 150 engaging the flash plug 128. This lock 155 may be the first lock engaged in a multi-step locking arrangement. The first lock 155 is made possible based on a lock mechanism 152 located on the needle guard 108 that engages a first lock triangle 154 that is present in the needle housing 106. Other types of locks or lock locations may be possible as well. Further, an initial locking configuration prior to urging fluid from the flash chamber 118, such as lock 155, is not present in various embodiments. For example, certain embodiments may not lock the needle housing 106 until the needle 104 is fully retracted.

Upon further needle retraction, when the push feature 150 contacts the flash plug 128, the safety needle assembly 100 forces the fluid from the flash chamber 118, through the insertion needle 104 and into the sample collection reservoir 140. Specifically, as the insertion needle 104 is withdrawn into the needle guard 108, the rigid push feature 150 engages the proximal portion of the porous barrier comprising the flash plug 128 in the flash chamber 118. As this engagement and the needle retraction movement occurs, the flash plug 128 (i.e. porous barrier) is forced into the flash chamber 118 by the rigid push feature 150. The flash plug 128 acts like a plunger to force the fluid sample into the collection reservoir 140. Because the needle assembly 100 can be designed with a push feature 150 sized for a desired fluid volume displacement from the flash chamber 118, the amount of fluid provided to the sample collection reservoir 140 can accordingly be well-controlled and suitable amounts of fluid made available via the reservoir 140 for sampling.

Referring to FIG. 8, the safety needle assembly 100 is shown where the collection reservoir has been filled and the insertion needle 104 has moved proximally to a fully retracted position (i.e. "second retracted position" or "fully retracted position"). In this position, the insertion needle 104 can be safely locked within needle guard 108 as shown. Specifically, within the needle guard 108, the sharpened distal tip 110 of the insertion needle 104 is fully contained within the nose 134. Further, the needle housing 106 has been moved to the proximal portion of needle guard 108 and the push feature 150 is shown in contact with the flash plug 128 such that flash plug 128 has been urged partially into the cavity 122 of flash chamber 118. This urging has caused plunging of fluid down the insertion needle 104 from the flash chamber 118 into the fluid collection reservoir 140.

In terms of locking arrangements, the lock mechanism 152 on the needle guard 108 is shown interacting with a second lock triangle 156 that is present on the needle housing 106, to provide a second lock 157. It should be understood, however, that embodiments containing only a single lock (i.e. only containing a lock 157 in the fully retracted position) are contemplated by these figures and disclosure as well. In general, second lock 157 restricts distal movement of the needle housing 106 after the push feature 150 engages the flash plug 128 and diverts captured bodily fluids to the fluid collection reservoir 140 for sampling.

Accordingly, a two step locking arrangement is made possible for restricting distal movement of the needle housing 106 that includes a first lock 155 and a second lock 157. Needle retraction, accordingly, can be split into a two step process so that a user can either elect to merely safely retract the insertion needle 104 or to retract the insertion needle 104 and additionally fill the collection reservoir 140 of the nose extension 102 for diagnostic sampling as well. This split process enables a user input on whether a diagnostics fluid sample is desired. The first step retracts the insertion needle 104 in a normal fashion without filling the reservoir with fluid. For users who do not wish to sample the fluid of the flash chamber 118, this is the final step. For users who wish to sample the fluid, a second action will be completed to further advance the insertion needle 104 to a point where the push feature 150 contacts and moves the flash plug 128.

In some embodiments, engaging the second lock 157 will be deigned to require a different type of user motion than required to engage the first lock 155. For example in addition to a linear proximal movement to engage a first lock 155, a rotation or similar movement could engage the second lock 157. This type arrangement could help avoid unintentional preliminary locking of the needle assembly 100. In certain embodiments, needle retraction will be designed to include filling of a collection reservoir 140 of the nose extension 102 by default and merely rely on a second lock 157 without the inclusion of a first lock 155. In such embodiments, retraction of the needle housing 106 will automatically provide fluid in the collection reservoir 140 that is available for distribution and sampling.

Figure 9:
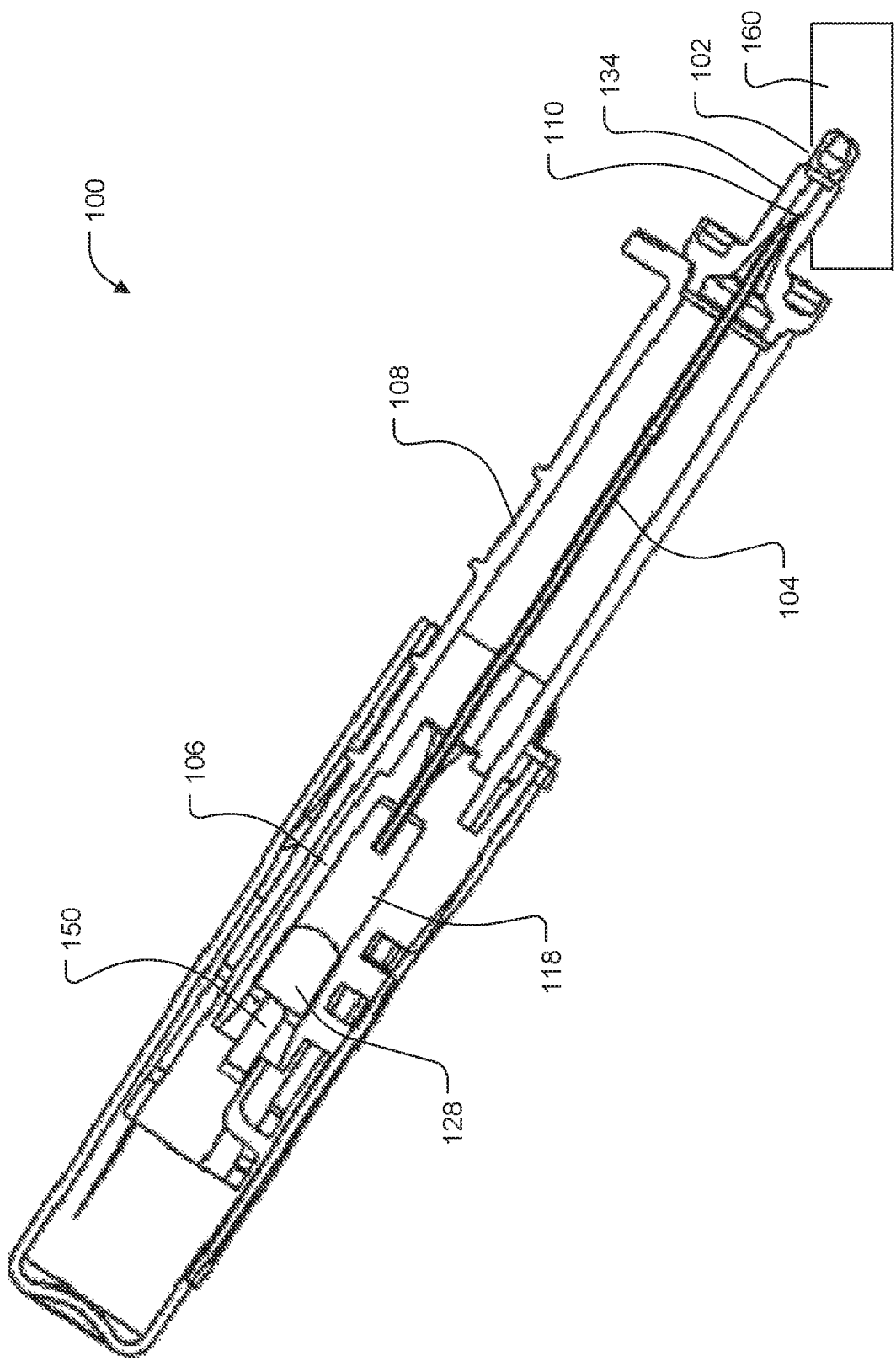
FIG. 9 is a side cross sectional view depicting a safety needle assembly where the needle is in a fully retracted position and the fluid of the collection reservoir is being accessed, according to an embodiment.

As shown in FIG. 9, the safety needle assembly 100 provides easy sampling of fluid from a filled collection reservoir 140 inside nose extension 102 to a test strip 160. Specifically, the fluid inside collection reservoir 140 can be accessed by pressing the flexible tip of the nose extension 102 inward from the side, for example. This side pressure opens the distal tip outer seal 142 and allows access to the fluid sample, such as by controlled expression of drops of blood or fluid. Some embodiments, the nose extension 102 can be pressed against a sampling strip 160 or other sampling item's surface to distort a wall 141 of the nose extension 102 to open the distal tip outer seal 142. Accordingly, one or more drops of blood or fluid can be deposited in a highly controlled manner. For example, embodiments may utilize fluid sampling strips 160, such as a blood glucose monitoring test strip or other similar test strip, device or mechanism. Permitting access to fluids in this way enables a high level of control and accuracy to fluid sampling.

In general, a needle assembly 100 can therefore be used, in operation, to sample a bodily fluid from a patient In one operation, a needle assembly 100 is provided that includes: a needle guard 108 including a flexible nose extension 102 defining a fluid collection reservoir 140 at a distal end 130 of the needle guard 108 and a push feature 150 at a proximal end 132 of the needle guard 108; an insertion needle 104 having a lumen 116 and a sharpened distal tip 110; and a needle housing 106 operably coupled to a proximal end 112 of the insertion needle 104 and slideably coupled to the needle guard 108 where the needle housing 106 includes a flash chamber 118 in fluid communication with the insertion needle 104 and is sealed at one end by a flash plug 128.

Next, in this operation, the insertion needle 104 is inserted in the patient to access bodily fluid that is provided through the lumen 116 to the flash chamber 118 and retracting the needle housing 106 until the sharpened distal tip 110 of the insertion needle 104 is located within the needle guard 108. Additionally, the needle housing 106 is retracted so that the push feature 150 contacts the flash plug 128 of the flash chamber 118 and provides the bodily fluid back out the lumen 116 into the fluid collection reservoir 140 of the flexible nose extension 102. Next, the flexible nose extension 102 is distorted to open a seal 142 and express the bodily fluid of the fluid collection reservoir 140 in a controlled fashion.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A needle assembly for sampling fluid from a patient, comprising:
   a needle guard having a distal end and a proximal end, the distal end of the needle guard including a nose portion and a flexible nose extension that defines a deformable fluid collection reservoir including an outer seal, the proximal end of the needle guard including a push feature;
   an insertion needle having a sharpened distal tip, a proximal needle end and a shaft defining a lumen extending therebetween; and
   a needle housing operably coupled to the proximal needle end and slideably coupled to the needle guard, the needle housing including a flash chamber comprising a wall defining a cavity, the cavity in fluid communication with the lumen of the insertion needle and sealed at one end by a gas permeable flash plug;
   wherein the needle housing is moveable between an extended position in which the sharpened distal tip is exposed for insertion and one or more retracted positions in which the sharpened distal tip is concealed within the needle guard;
   wherein the push feature is selectively engagable with the flash plug to urge captured bodily fluids from the flash chamber into the fluid collection reservoir, when the needle housing is in one of the one or more retracted positions; and
   wherein the bodily fluid in the fluid collection reservoir is accessible by applying an external pressure to the flexible nose extension, so as to deform the fluid collection reservoir and open the outer seal for expression of at least a portion of the bodily fluid therein.

2. The needle assembly of claim 1, further comprising:
   a lock mechanism that is configured to restrict distal movement of the needle housing after the push feature engages the flash plug and urge captured bodily fluids to the fluid collection reservoir.

3. The needle assembly of claim 1, further comprising a two step locking arrangement for restricting distal movement of the needle housing that includes a first lock and a second lock.

4. The needle assembly of claim 3, wherein the first lock is configured to restrict distal movement of the needle housing relative to the needle guard prior to the push feature engaging the flash plug and wherein the second lock is configured to restrict distal movement of the needle housing relative to the needle guard after the push feature has engaged the flash plug and diverted captured bodily fluids to the fluid collection reservoir for sampling.

5. The needle assembly of claim 4, wherein the first lock is configured to be engaged with a first type of user motion; and the second lock is configured to be engaged with a second type of user motion.

6. The needle assembly of claim 1, wherein the one or more retracted positions include a partially retracted position and a fully retracted position.

7. The needle assembly of claim 6, wherein the needle housing is moveable in a proximal direction between:
   the extended position;
   the partially retracted position wherein the sharpened distal tip of the insertion needle is withdrawn into the needle guard and the push feature has not yet begun to engage the flash plug; and
   the fully retracted position in which the push feature has engaged the flash plug and urged fluid from the flash chamber into the fluid collection reservoir of the flexible nose extension and the needle housing is prevented from further sliding movement.

8. The needle assembly of claim 1, wherein a catheter hub is operably coupled to the nose portion of the needle guard in the extended position.

* * * * *